United States Patent
Ritzdorf et al.

(10) Patent No.: US 8,267,880 B2
(45) Date of Patent: Sep. 18, 2012

(54) ELASTIC BANDAGE SEGMENT

(75) Inventors: Gerd Ritzdorf, Hammerstein (DE); Thomas Hill, Neuwied (DE)

(73) Assignee: Paul Hartmann AG, Heidenheim (DE)

( * ) Notice: Subject to any disclaimer, the term of this patent is extended or adjusted under 35 U.S.C. 154(b) by 80 days.

(21) Appl. No.: 10/598,710

(22) PCT Filed: Mar. 9, 2005

(86) PCT No.: PCT/EP2005/002451
§ 371 (c)(1),
(2), (4) Date: Sep. 8, 2006

(87) PCT Pub. No.: WO2005/087159
PCT Pub. Date: Sep. 22, 2005

(65) Prior Publication Data
US 2007/0179418 A1    Aug. 2, 2007

(30) Foreign Application Priority Data
Mar. 13, 2004   (DE) .......................... 10 2004 012 442

(51) Int. Cl.
*A61F 13/00* (2006.01)
(52) U.S. Cl. ................ 602/75; 602/41; 602/42; 602/53; 602/76
(58) Field of Classification Search ............. 602/54, 602/41–43, 74–79, 52
See application file for complete search history.

(56) References Cited

U.S. PATENT DOCUMENTS

| | | | | | |
|---|---|---|---|---|---|
| 3,618,754 A | * | 11/1971 | Hoey | .......................... | 206/411 |
| 3,710,599 A | * | 1/1973 | Sarmiento | ....................... | 66/193 |
| 4,366,814 A | * | 1/1983 | Riedel | .............................. | 602/77 |
| 4,424,808 A | * | 1/1984 | Schafer et al. | .................. | 602/76 |
| 4,875,476 A | | 10/1989 | Garcia | | |
| 5,397,298 A | * | 3/1995 | Mazza et al. | .................... | 602/75 |
| 5,540,922 A | * | 7/1996 | Fabo | ............................. | 424/402 |
| 5,749,843 A | | 5/1998 | Miller | | |
| 6,051,747 A | * | 4/2000 | Lindqvist et al. | .............. | 602/46 |
| 6,063,048 A | * | 5/2000 | Bodenschatz et al. | .......... | 602/62 |
| 2007/0202245 A1 | * | 8/2007 | Gantner et al. | ............... | 427/2.1 |

FOREIGN PATENT DOCUMENTS

| | | |
|---|---|---|
| DE | 3305408 | 11/1986 |
| DE | 3843483 | 6/1990 |
| DE | 3931550 | 4/1991 |
| DE | 4312655 | 10/1994 |

(Continued)

OTHER PUBLICATIONS

Official Report (translation) from parallel JP 2007-502280 mailed Jun. 19, 2012.

*Primary Examiner* — Kim M Lewis
(74) *Attorney, Agent, or Firm* — Frommer Lawrence & Haug LLP

(57) ABSTRACT

The invention relates to an elastic adhesive unidirectional bandage and to a method for the production and the use thereof. The inventive bandage is embodied in the form of a segment, exhibits elastic and adhesive properties and is designed, in particular for supporting joints and preventing and maximally reducing injuries in certain body regions. The bandage segment is held in position during a long time by means of the adhesive properties thereof and supports natural movements by the elasticity thereof without constrictions and folds. Even, when the bandage is carried for a long time, it does not provoke a foreign body feeling. The bandage segment is easily applicable and optimally anatomically adaptable by the specific design of the elastic areas (for example, only the partial areas of the segment are elastic) and by corresponding shape thereof.

18 Claims, 1 Drawing Sheet

FOREIGN PATENT DOCUMENTS

Figure 1A:
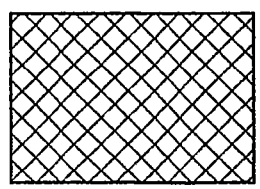

| | | |
|---|---|---|
| DE | 19738855 | 3/1999 |
| DE | 19819442 | 11/1999 |
| DE | 10101530 | 7/2002 |
| EP | 0099010 | 6/1983 |
| EP | 0670705 | 9/1995 |
| EP | 0779064 | 6/1997 |
| JP | S60-163907 | 10/1985 |
| JP | 2674030 | 3/1989 |
| JP | 03-070558 | 3/1991 |
| JP | H03-70558 | 3/1991 |
| JP | 03-254744 | 11/1991 |
| JP | 08019568 | 1/1996 |
| JP | 8191856 | 7/1996 |
| JP | 2000051264 | 2/2000 |
| JP | 2001-37803 | 2/2001 |
| JP | 3081179 | 10/2001 |
| JP | 2003290272 | 10/2003 |
| JP | 2003535647 | 12/2003 |
| JP | 2004049543 | 2/2004 |
| WO | WO 91/01704 | 10/1991 |
| WO | WO 95/06449 | 3/1995 |
| WO | WO 99/16396 | 4/1999 |

\* cited by examiner

ELASTIC BANDAGE SEGMENT

The invention relates to a bandage segment comprising a backing layer made of a unidirectionally elastic woven fabric, an adhesive layer, and a releasable protective layer. The invention also relates to a method for producing bandage segments of this kind, and to their use.

To prevent and minimize injuries to the joints, for example the knees, ankles, wrists, finger joints or parts of the locomotor apparatus, support dressings are used which take account of the changing requirements arising in sports activities for example.

Adhesive and nonadhesive elastic bandages are known, for example the commercially available product called Porelastacryl, a skin-colored plaster made of longitudinally elastic cotton fabric coated with a hypoallergenic polyacrylate adhesive. A disadvantage of these elastic bandages is that, if they are not coated with adhesive, they either slip and fail to remain in their original position as a result of movement and in so doing lose their function. Or, if they are indeed coated with adhesive, they can cause blood vessel constrictions during application. In addition, these bandages are often difficult for medically untrained persons to apply, and they require a special dressing technique.

WO 99/016396 describes an elastic adhesive dressing of high elasticity in the shape of a boomerang which is applied to parts of the body with very pronounced curves, without the skin being exposed to significant stresses after application. The formation of folds after application is intended to be prevented by this means. However, the high elasticity means that the joint is not supported.

Therefore, the object of the invention is to make available such a support bandage which avoids the aforementioned disadvantages and is easy to use.

According to the invention, the object is achieved by a bandage segment having an adhesive backing layer which has a specially defined unidirectional elasticity and which is covered by a releasable protective layer. A bandage segment such as this is a medical product which is to be applied to the skin and which has the appearance of traditional plasters. In contrast to these, it is not affixed to open wounds. The fact that the bandage segment is not wound round the joint like conventional bandages means it is not possible for constriction to occur. At the same time, the elastic behavior of the bandage segment means that the joint is permanently supported, including during movements. A particular advantage of the bandage segments is that they can also easily be applied by persons who are not medically trained, and they do not cause a foreign-body sensation, even when worn over a fairly long period of time, for example when participating in sport.

The bandage segment according to the invention is shown in the preferred embodiments in FIGS. 1-3, where the hatched areas shown in the drawings represent the elastic areas.

Figure 1B:
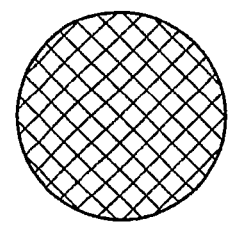

Other preferred embodiments are the subject of the dependent claims. This means that the backing layer comprises a unidirectional, in particular transversely elastic material with an elasticity of at least 20%. The bandage segments preferably have a rectangular shape, and a size with a side ratio of length to width of 1.2:1 to 1.8:1, similar to post cards or check cards, as depicted in FIG. 1a. However, round shapes, as shown in FIG. 1b, and shapes adapted to the particular anatomy are also possible.

Figure 2A:
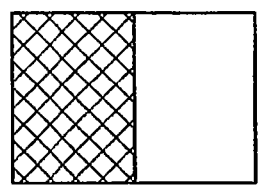
Figure 2B:
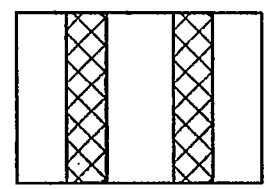

Further configurations of the bandage segment according to the invention for which protection is claimed are bandage segments, as shown in FIGS. 2a and 2b, in which only a partial area of the segment is made elastic. For example, only a central area is elastic, and the two edge areas are nonelastic. Further embodiments are those in which two or more central areas are elastic, and the two edge areas and the areas lying between the elastic areas are nonelastic. A bandage segment is thus obtained which alternately has elastic and nonelastic areas, the distance between the elastic areas depending on the application. By means of this arrangement, the desired support effect can be achieved both via the elasticity of the bandage segment and also via the size of the elastic areas.

Figure 3A:
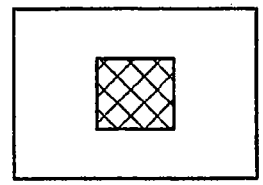
Figure 3B:
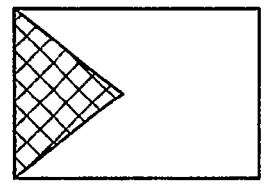
Figure 3C:
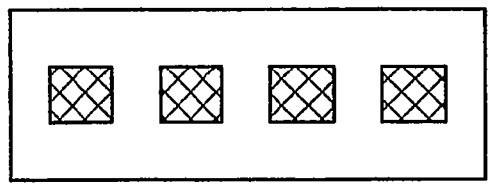

The elastic areas can also be configured such that they are surrounded completely or at least substantially by nonelastic areas, as is shown in FIGS. 3a, 3b and 3c. The elastic areas can be of any desired shape, the latter depending on the particular area that is to be supported. An advantageous embodiment of the bandage segment is shown in FIG. 3c with several elastic areas arranged alongside one another or behind one another at a defined spacing for simultaneously supporting all the joints, for example between the metacarpal bones and the bones of the fingers.

In the bandage according to the invention, the elasticity is determined according to the DIN standards used in elasticity tests, namely DIN 60000 and 61632 (in the version of April 1985). These DIN standards originally applied for Ideal Bandages, but the horizontal stress elongation equipment used for testing elasticity can also be applied analogously for other materials.

According to the invention, the backing layer of the bandage is elastic only in one direction, i.e. in the longitudinal direction or transverse direction. Relative to the longitudinal axis of the bandage, the transverse axis is the axis lying at right angles thereto. The other direction of the backing layer is nonelastic. "Nonelastic" means that no elasticity can be determined when testing by hand. When measured according to DIN 61632, the elasticity then lies below 20%. According to the invention, the elasticity in one direction, namely the elastic direction, is over 20%.

In the bandage according to the invention, the elastic material used for the backing layer is preferably one whose elasticity is less than 150%. In a more preferred embodiment, the elasticity lies in the range of 20 to 80%, particularly preferably in the range of between 40 and 70%. The most preferred embodiment, and therefore the most advantageous one for achieving the object of the invention, is for the backing layer to be made of a material whose elasticity, again measured according to DIN 61632, is in the range of between 44 and 56%.

Preferred materials for the unidirectional elastic backing layer are microbiologically nondegradable substances. The material should be microbiologically nondegradable to an extent of more than 90% and preferably to an extent of more than 99%. The degradability can be measured by conventional methods familiar to the person skilled in the art. The low degradability is particularly important in medical products used in the dermal region, which are worn on the skin for longer. Due to the transpiration of the skin, a microclimate is created directly underneath the skin region covered by the bandage, and bacteria, fungi, spores, etc., thrive in this microclimate. A low level of microbiological degradability is therefore extremely advantageous, especially in cases where the bandages are worn for quite a long time. In addition, the materials used for the backing layer are preferably breathable and allow water vapor to pass through them.

The material of the backing layer can be a woven fabric, a film or a combination of both, e.g. made of viscose, polyester, polyamide, cotton or elastane. If the backing layer comprises a polymer, this is advantageously chosen from polyethylene, polypropylene or polyester, in particular polyalkylene terephthalates.

The following are a few examples of polymer materials for the backing layer. Suitable polymer materials meeting the above requirements of low microbiological degradability are polyterephthalates obtainable by conversion of starting substances chosen from ethylene glycol, 1,4-butanediol, 1,4-dihydroxymethyl cyclohexane, terephthalic acid, isophthalic acid, adipic acid, azelaic acid, sebacic acid, phthalic acid, bisphenol A diglycidyl ether, n-decane-1,10-dioic acid, polyethylene glycol and polybutylene glycol.

In the case where a film is used, the porosity is in the range of 10 to 50%. Here, "porosity" means pores covering a surface area of >400 µm$^2$ on the respective reference surface. This relative pore surface can be determined by measuring and counting the pores on an unstretched reference surface under a microscope or a thread counter. If a woven fabric is used for the bandage according to the invention, the backing layer has a warp number in the range of 300-350, preferably in the range of 310-330, and a weft number in the range of 100-140, preferably in the range of 120-130, in each case measured per 10 cm of unstretched woven fabric.

The adhesive layer is composed of self-adhering polymers selected from the group of polyacrylates, silicones, polyisobutylenes and the like. Since the bandage segment is fixed on the skin directly by the adhesive, it goes without saying that the adhesion force of the adhesive layer must be much greater than in the case of adhesive-coated, elastic bandages which are fixed by bonding of the films. Particular preference is given to adhesive layers which, measured at a length of 25 mm, have an adhesion force of 0.1 to 100 N, particularly preferably 1 to 10 N, the adhesive being applied across the whole surface of or at least on a part of the underside of the carrier and/or in the form of patterns, for example in dots or grids.

The bandage according to the invention is produced using customary methods. One such method generally includes the steps of coating a silicone-treated paper with an adhesive-containing solution. Any solvent present is removed by drying in a drying tunnel. The laminate, composed of releasable paper or film and adhesive layer, is then covered with the unidirectionally elastic backing layer.

This production step can be followed by cutting into narrow rolls from which the segments are punched or cut out by methods known to the person skilled in the art. However, it is also possible, according to the invention, to produce the segments from the laminate in the form of a wide roll, known to the person skilled in the art as a jumbo roll or master roll. The bandage segments are then formatted using a suitable punching tool, and packaged individually in cartons.

The invention is explained below on the basis of an illustrative embodiment:

Example: To produce the unidirectional elastic backing layer according to the invention, a woven polyester fabric with the following features, shown in Table 1, was produced using techniques known to the person skilled in the art.

TABLE 1

| Test features | Unit | Target | Min | Max | Mean |
|---|---|---|---|---|---|
| Width | mm | 1580 | 800 | 1600 | 1580 |
| Weight per unit area (unstretched) (DIN 53854 + DIN 53884) | g/m$^2$ | 100 | 95 | 103 | 100 |
| Elongation (longitudinal) | % | | | | |
| (transverse) (DIN 61632) | % | 50 | 46 | 52 | 48 |
| Warp number 10 cm unstretched | | 320 | 310 | 330 | 324 |
| Weft number 10 cm unstretched | | 125 | 124 | 126 | 124 |

In addition 581 kg Durotak 387-2051 (52% strength solution)

48 kg ethanol and 0.6 kg aluminum acetylacetonate were homogenized by stirring.

Stirring was carried out for ca. 18 hours at 56 rpm. This was followed by a homogeneity test. If the composition was homogeneous, it was allowed to stand with the agitator switched off. In this way the adhesive solution was freed of air bubbles.

After homogenization, the adhesive composition was painted onto a silicone-treated paper. The organic solvents were removed by drying at the customary 35 to 80° C. The laminate of silicone-treated paper and adhesive layer was then covered with a unidirectionally elastic woven polyester fabric according to Table 1. From the laminate thus obtained, the bandage segments were punched out to a format measuring 60×90 mm.

The invention claimed is:

1. A unidirectionally elastic bandage, with adhesive on one side, for supporting joints, comprising:
    a backing layer which is unidirectionally elastic in one direction selected from the group consisting of a longitudinal direction and a transverse direction and non-elastic in the other direction;
    an adhesive layer, and
    a releasable protective layer;
    characterized in that the bandage is embodied as a segment with the backing layer having elastic areas and has an elasticity in the elastic areas of the backing layer in the range of 20% to 150%;
    characterized in that the bandage segment is transversely elastic or longitudinally elastic;
    characterized in that the adhesive is applied across an entire surface of backing layer or on a part of an underside of the backing layer or in the form of patterns; and
    characterized in that one or more defined areas of the segment are elastic and the segment also contains non-elastic areas, wherein the one or more defined areas of the segment which are elastic are surrounded by non-elastic areas.

2. The unidirectionally elastic adhesive bandage as claimed in claim 1, characterized in that the elasticity of the backing layer lies in the range of between 20% and 80%.

3. The unidirectionally elastic adhesive bandage as claimed in claim 2, characterized in that the elasticity of the backing layer lies in the range of between 40% and 70%.

4. The unidirectionally elastic adhesive bandage as claimed in claim 3, characterized in that the elasticity of the backing layer lies in the range of between 44% and 56%.

5. The unidirectionally elastic adhesive bandage as claimed in claim 1, characterized in that the adhesive composed of self-adhesive polymers is selected from the group consisting of polyacrylates, silicones and polyisobutylenes.

6. The unidirectionally elastic adhesive bandage as claimed in claim 5, characterized in that the elasticity of the backing layer lies in the range of between 44% and 56%.

7. The unidirectionally elastic adhesive bandage as claimed in claim 6, characterized in that the backing layer is microbiologically nondegradable to an extent of more than 90%.

8. The unidirectionally elastic adhesive bandage as claimed in claim 7, characterized in that the backing layer is microbiologically nondegradable to an extent of more than 99%.

9. The unidirectionally elastic adhesive bandage as claimed in claim 7, characterized in that of the backing layer is a woven fabric or a film or a combination of both made from viscose, polyester, polyamide, cotton or elastane.

10. The unidirectionally elastic adhesive bandage as claimed in claim 9, characterized in that the backing layer is a polymer material is selected from the group consisting of polyethylene, polypropylene and polyester.

11. The unidirectionally elastic adhesive bandage as claimed in claim 10, characterized in that the material of the backing layer is polyalkylene terephthalates.

12. The unidirectionally elastic adhesive bandage as claimed in claim 9, characterized in that the porosity of the film is in the range of 10 to 50%.

13. The unidirectionally elastic adhesive bandage as claimed in claim 9, characterized in that the backing layer has a warp number in the range of 300-350, and a weft number in the range of 100-140.

14. The unidirectionally elastic adhesive bandage as claimed in claim 13, characterized in that the backing layer has a warp number in the range of 310-330 and a weft number in the range of 120-130.

15. The unidirectionally elastic adhesive bandage as claimed in claim 1, characterized in that the backing layer is breathable and allows water vapor to pass through.

16. The unidirectionally elastic adhesive bandage as claimed in claim 1, characterized in that the bandage segment is rectangular with a side ratio of length to width of 1.2:1 to 1.8:1.

17. A method for producing unidirectionally elastic adhesive bandage comprising the steps of: providing a unidirectionally elastic bandage, with adhesive on one side, for supporting joints, comprising: a backing layer which is unidirectionally elastic in one direction selected from the group consisting of a longitudinal direction and a transverse direction and non-elastic in the other direction; an adhesive layer, and a releasable protective layer; characterized in that the bandage is embodied as a segment with the backing layer having elastic areas and has an elasticity in the elastic areas of the backing layer in the range of 20% to 150%; characterized in that the bandage segment is transversely elastic or longitudinally elastic; characterized in that the adhesive is applied across an entire surface of backing layer or on a part of an underside of the backing layer or in the form of patterns; and characterized in that one or more defined areas of the segment are elastic and the segment also contains non-elastic areas, wherein the one or more defined areas of the segment which are elastic are surrounded by non-elastic areas;

coating silicone-treated paper/film with an adhesive-containing solution;

covering the laminate of releasable paper/film and adhesive layer with the unidirectionally elastic backing layer; and punching the bandage segments out from narrow or wide rolls of the laminate.

18. The unidirectionally elastic adhesive bandage as claimed in claim 14, characterized in that the bandage segment is rectangular with a side ratio of length to width of 1.2:1 to 1.8:1.

* * * * *